US010369256B2

(12) United States Patent
Flanagan et al.

(10) Patent No.: US 10,369,256 B2
(45) Date of Patent: Aug. 6, 2019

(54) USE OF NANOCRYSTALS FOR DRUG DELIVERY FROM A BALLOON (75) Inventors: Aiden Flanagan, Galway (IE); Jan Weber, Maastricht (NL); John Clarke, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 444 days.

(21) Appl. No.: 12/815,158

(22) Filed: Jun. 14, 2010

(65) Prior Publication Data

US 2011/0008260 A1 Jan. 13, 2011

Related U.S. Application Data (60) Provisional application No. 61/224,723, filed on Jul. 10, 2009.

(51) Int. Cl.
A61F 2/06 (2013.01)
A61L 29/16 (2006.01)

(52) U.S. Cl.
CPC ......... *A61L 29/16* (2013.01); *A61L 2300/416* (2013.01); *A61L 2300/624* (2013.01); *A61L 2300/63* (2013.01)

(58) Field of Classification Search
CPC ........ A61F 2/00; A61F 2/0013; A61F 2/0022; A61F 2/063; A61F 2/0077; A61F 2/01
USPC ........................................ 424/489, 448, 465
See application file for complete search history.

(56) References Cited

U.S. PATENT DOCUMENTS

| | | |
|---|---|---|
| 304,121 A | 8/1884 | Munch |
| 4,026,296 A | 5/1977 | Stoy |
| 4,186,745 A | 2/1980 | Lewis |
| 4,364,392 A | 12/1982 | Strother et al. |
| 4,481,323 A | 11/1984 | Sterling |
| 4,490,421 A | 12/1984 | Levy |
| 4,515,593 A | 5/1985 | Norton |
| 4,589,873 A | 5/1986 | Schwartz |
| 4,603,152 A | 7/1986 | Laurin |
| 4,644,936 A | 2/1987 | Schiff |
| 4,693,243 A | 9/1987 | Buras |
| 4,733,665 A | 3/1988 | Palmaz |
| 4,769,013 A | 9/1988 | Lorenz |
| 4,784,647 A | 11/1988 | Gross |
| 4,796,629 A | 1/1989 | Grayzel |
| 4,800,882 A | 1/1989 | Gianturco |
| 4,886,062 A | 12/1989 | Wiktor |
| 4,906,244 A | 3/1990 | Pinchuk et al. |
| 4,931,583 A | 6/1990 | Hull et al. |
| 4,950,239 A | 8/1990 | Gahara |
| 4,950,256 A | 8/1990 | Luther |
| 4,994,033 A | 2/1991 | Shockey et al. |
| 5,026,607 A | 6/1991 | Kiezulas |
| 5,027,996 A | 7/1991 | Fefeu |
| 5,041,100 A | 8/1991 | Rowland |
| 5,049,131 A | 9/1991 | Deuss |
| 5,087,244 A | 2/1992 | Wolinsky et al. |
| 5,091,205 A | 2/1992 | Fan |
| 2,098,381 A | 3/1992 | Schneider |
| 5,092,841 A | 3/1992 | Spears |
| 5,098,381 A | 3/1992 | Schneider |
| 5,102,402 A * | 4/1992 | Dror et al. ..................... 604/265 |
| 5,135,516 A | 8/1992 | Sahatjian |
| 5,169,933 A | 12/1992 | Anderson |
| 5,180,366 A | 1/1993 | Woods |
| 5,199,951 A | 4/1993 | Spears |
| 5,213,576 A | 5/1993 | Abiuso et al. |
| 5,213,580 A | 5/1993 | Slepian et al. |
| 5,232,444 A | 8/1993 | Just et al. |
| 5,236,413 A | 8/1993 | Feiring |
| 5,250,069 A | 10/1993 | Nobuyoshi |
| 5,264,260 A | 11/1993 | Saab |
| 5,270,086 A | 12/1993 | Hamlin |
| 5,282,785 A | 2/1994 | Shapland et al. |
| 5,286,254 A | 2/1994 | Shapland et al. |
| 5,295,962 A | 3/1994 | Crocker et al. |
| 5,304,121 A | 4/1994 | Sahatjian |
| 5,318,531 A | 6/1994 | Leone |
| 5,320,634 A | 6/1994 | Vigil |
| 5,324,261 A | 6/1994 | Amundson et al. |
| 5,328,468 A | 7/1994 | Kaneko |
| 5,328,471 A | 7/1994 | Slepian |
| 5,342,628 A | 8/1994 | Picha |
| 5,344,400 A | 9/1994 | Kaneko |

(Continued)

FOREIGN PATENT DOCUMENTS

| | | |
|---|---|---|
| CA | 2363119 | 8/2000 |
| DE | 19908318 | 8/2000 |

(Continued)

OTHER PUBLICATIONS

R. Charles, et al, "Ceramide-Coated Balloon Catheters Limit Neointimal Hyperplasia After Stretch Injury in Cartoid Arteries," Circ. Res. 2000;87;282-288.
D. Mastropaolo, et al, "Crystal and molecular structure of paclitaxel (taxol)," Proc. Natl. Acad. Sci. USA, 92, pp. 6920-6924 (Jul. 1995).
U.S. Appl. No. 61/322,451, filed Apr. 9, 2010.
U.S. Appl. No. 61/330,201, filed Apr. 30, 2010.
U.S. Appl. No. 61/332,544, filed Apr. 9, 2010.
U.S. Appl. No. 61/352,117, filed Jun. 7, 2010.
U.S. Appl. No. 61/379,608, filed Sep. 2, 2010.
U.S. Appl. No. 61/385,849, filed Sep. 23, 2010.
U.S. Appl. No. 61/394,104, filed Oct. 18, 2010.
U.S. Appl. No. 61/421,054, filed Dec. 8, 2010.

(Continued)

*Primary Examiner* — Micah Paul Young
(74) *Attorney, Agent, or Firm* — Seager, Tufte & Wickhem, LLP (57) ABSTRACT

A drug delivery balloon (10) has a drug thereon in the form of crystalline particles (12), the drug having a predetermined size distribution. Optionally marker particles (14, 16) are also provided. A texturized coating (18), a cap layer (20) and/or other methods may be used to increase particle loading capacity of the balloon.

12 Claims, 2 Drawing Sheets

(56) References Cited

U.S. PATENT DOCUMENTS

| | | |
|---|---|---|
| 5,344,402 A | 9/1994 | Crocker |
| 5,362,831 A | 11/1994 | Mongelli |
| 5,368,566 A | 11/1994 | Crocker |
| 5,370,614 A | 12/1994 | Amundson et al. |
| 5,380,299 A | 1/1995 | Fearnot |
| 5,383,928 A | 1/1995 | Scott |
| 5,385,152 A | 1/1995 | Abele |
| 5,405,472 A | 4/1995 | Leone |
| 5,419,760 A | 5/1995 | Narciso |
| 5,421,826 A | 6/1995 | Crocker et al. |
| 5,425,703 A | 6/1995 | Feiring |
| 5,427,767 A | 6/1995 | Kresse |
| 5,439,446 A | 8/1995 | Barry |
| 5,443,496 A | 8/1995 | Schwartz |
| 5,447,724 A | 9/1995 | Helmus |
| 5,449,382 A | 9/1995 | Dayton |
| 5,464,650 A | 11/1995 | Berg |
| 5,470,307 A | 11/1995 | Lindall |
| 5,489,525 A | 2/1996 | Pastan |
| 5,498,238 A | 3/1996 | Shapland et al. |
| 5,499,971 A | 3/1996 | Shapland et al. |
| 5,500,180 A | 3/1996 | Anderson |
| 5,542,926 A | 8/1996 | Crocker |
| 5,545,208 A | 8/1996 | Wolff |
| 5,549,603 A | 8/1996 | Feiring |
| 5,554,119 A | 9/1996 | Harrison et al. |
| 5,554,182 A | 9/1996 | Dinh |
| 5,556,383 A | 9/1996 | Wang et al. |
| 5,558,642 A | 9/1996 | Schweich, Jr. et al. |
| 5,562,922 A | 10/1996 | Lambert |
| 5,569,184 A | 10/1996 | Crocker et al. |
| 5,569,463 A | 10/1996 | Helmus |
| 5,571,089 A | 11/1996 | Crocker |
| 5,578,075 A | 11/1996 | Dayton |
| 5,588,962 A | 12/1996 | Nicholas et al. |
| 5,599,306 A | 2/1997 | Klein et al. |
| 5,599,307 A | 2/1997 | Bacher et al. |
| 5,609,629 A | 3/1997 | Fearnot et al. |
| 5,611,775 A | 3/1997 | Machold et al. |
| 5,616,149 A | 4/1997 | Barath |
| 5,624,411 A | 4/1997 | Tuch |
| 5,626,862 A | 5/1997 | Brem |
| 5,628,730 A | 5/1997 | Shapland et al. |
| 5,629,008 A | 5/1997 | Lee |
| 5,634,901 A | 6/1997 | Alba |
| 5,637,086 A | 6/1997 | Ferguson et al. |
| 5,651,986 A | 7/1997 | Brem |
| 5,665,772 A | 9/1997 | Cottens |
| 5,669,874 A | 9/1997 | Feiring |
| 5,674,192 A | 10/1997 | Sahatjian et al. |
| 5,674,241 A | 10/1997 | Bley |
| 5,679,400 A | 11/1997 | Tuch |
| 5,685,847 A | 11/1997 | Barry |
| 5,688,516 A | 11/1997 | Raad |
| 5,693,034 A | 12/1997 | Buscemi et al. |
| 5,697,967 A | 12/1997 | Dinh |
| 5,704,908 A | 1/1998 | Hofmann et al. |
| 5,707,385 A | 1/1998 | Williams |
| 5,716,981 A | 2/1998 | Hunter |
| 5,728,066 A | 3/1998 | Daneshvar |
| 5,733,925 A | 3/1998 | Kunz |
| 5,766,158 A | 6/1998 | Opolski |
| 5,769,883 A | 6/1998 | Buscemi |
| 5,797,877 A | 8/1998 | Hamilton |
| 5,800,538 A | 9/1998 | Slepian et al. |
| 5,807,306 A | 9/1998 | Shapland et al. |
| 5,810,763 A | 9/1998 | Feiring |
| 5,833,657 A | 11/1998 | Reinhardt et al. |
| 5,833,658 A | 11/1998 | Levy |
| 5,843,089 A | 12/1998 | Sahatjian et al. |
| 5,854,382 A | 12/1998 | Loomis |
| 5,855,546 A | 1/1999 | Hastings |
| 5,857,998 A | 1/1999 | Barry |
| 5,865,801 A | 2/1999 | Houser |
| 5,868,719 A | 2/1999 | Tsukernik |
| 5,869,127 A | 2/1999 | Zhong |
| 5,876,374 A | 3/1999 | Alba |
| 5,893,840 A | 4/1999 | Hull et al. |
| 5,900,246 A | 5/1999 | Lambert |
| 5,902,266 A | 5/1999 | Leone |
| 5,902,299 A | 5/1999 | Jayaraman |
| 5,928,279 A | 7/1999 | Shannon |
| 5,935,275 A | 8/1999 | Burgard |
| 5,935,506 A | 8/1999 | Schmitz |
| 5,947,977 A | 9/1999 | Slepian et al. |
| 5,954,693 A | 9/1999 | Barry |
| 5,954,706 A | 9/1999 | Sahatjian |
| 5,977,163 A | 11/1999 | Li |
| 5,981,568 A | 11/1999 | Kunz et al. |
| 6,048,356 A | 4/2000 | Ravenscroft et al. |
| 6,048,515 A | 4/2000 | Kresse |
| 6,048,620 A | 4/2000 | Zhong |
| 6,099,454 A | 8/2000 | Hastings |
| 6,099,926 A | 8/2000 | Thakrar |
| 6,129,705 A | 10/2000 | Grantz |
| 6,142,973 A | 11/2000 | Carleton |
| 6,146,356 A | 11/2000 | Wang et al. |
| 6,146,358 A | 11/2000 | Rowe |
| 6,183,658 B1 | 2/2001 | Lesniak |
| 6,186,745 B1 | 2/2001 | Johnson |
| 6,195,583 B1 | 2/2001 | Feiring |
| 6,203,551 B1 | 3/2001 | Wu |
| 6,218,016 B1 | 4/2001 | Tedeschi et al. |
| 6,219,577 B1 | 4/2001 | Brown, III et al. |
| 6,240,407 B1 | 5/2001 | Chang |
| 6,245,103 B1 | 6/2001 | Stinson |
| 6,262,107 B1 | 7/2001 | Li |
| 6,270,522 B1 | 8/2001 | Simhambhatla |
| 6,280,411 B1 | 8/2001 | Lennox |
| 6,283,947 B1 | 9/2001 | Mirzaee |
| 6,287,332 B1 | 9/2001 | Bolz |
| 6,296,619 B1 | 10/2001 | Brisken et al. |
| 6,299,604 B1 | 10/2001 | Ragheb |
| 6,306,166 B1 | 10/2001 | Barry et al. |
| 6,344,028 B1 | 2/2002 | Barry |
| 6,355,029 B1 | 3/2002 | Joye |
| 6,364,856 B1 | 4/2002 | Ding et al. |
| 6,364,893 B1 | 4/2002 | Sahatjian et al. |
| 6,369,039 B1 | 4/2002 | Palasis et al. |
| 6,389,314 B2 | 5/2002 | Feiring |
| 6,391,033 B2 | 5/2002 | Ryan |
| 6,398,708 B1 | 6/2002 | Hastings |
| 6,409,716 B1 | 6/2002 | Sahatjian et al. |
| 6,418,448 B1 | 7/2002 | Sarkar |
| 6,419,692 B1 | 7/2002 | Yang et al. |
| 6,428,534 B1 | 8/2002 | Joye et al. |
| 6,432,102 B2 | 8/2002 | Joye |
| 6,440,990 B1 | 8/2002 | Cottens |
| 6,443,941 B1 | 9/2002 | Slepian et al. |
| 6,451,373 B1 | 9/2002 | Hossainy |
| 6,468,297 B1 | 10/2002 | Williams |
| 6,494,862 B1 | 12/2002 | Ray |
| 6,506,408 B1 | 1/2003 | Palasis |
| 6,511,477 B2 | 1/2003 | Altman |
| 6,514,245 B1 | 2/2003 | Williams |
| 6,524,274 B1 | 2/2003 | Rosenthal et al. |
| 6,527,740 B1 | 3/2003 | Jackson |
| 6,537,194 B1 | 3/2003 | Winkler |
| 6,541,039 B1 | 4/2003 | Lesniak |
| 6,544,221 B1 | 4/2003 | Kokish et al. |
| 6,544,223 B1 | 4/2003 | Kokish |
| 6,545,097 B2 | 4/2003 | Pinchuk et al. |
| 6,548,569 B1 | 4/2003 | Williams |
| 6,582,353 B1 | 6/2003 | Hastings |
| 6,585,926 B1 | 7/2003 | Mirzaee |
| 6,592,548 B2 | 7/2003 | Jayaraman |
| 6,602,246 B1 | 8/2003 | Joye |
| 6,616,650 B1 | 9/2003 | Rowe |
| 6,623,452 B2 | 9/2003 | Chien et al. |
| 6,623,749 B2 | 9/2003 | Williams |
| 6,638,246 B1 | 10/2003 | Naimark et al. |
| 6,645,135 B1 | 11/2003 | Bhat |
| 6,648,879 B2 | 11/2003 | Joye |
| 6,656,156 B2 | 12/2003 | Yang et al. |

(56) References Cited

U.S. PATENT DOCUMENTS

| | | |
|---|---|---|
| 6,663,880 B1 | 12/2003 | Roorda et al. |
| 6,682,545 B1 | 1/2004 | Kester |
| 6,685,648 B2 | 2/2004 | Flaherty |
| 6,699,272 B2 | 3/2004 | Slepian et al. |
| 6,706,013 B1 | 3/2004 | Bhat et al. |
| 6,730,105 B2 | 5/2004 | Shiber |
| 6,733,474 B2 | 5/2004 | Kusleika |
| 6,780,324 B2 | 8/2004 | Le Garrec et al. |
| 6,786,900 B2 | 9/2004 | Joye |
| 6,786,901 B2 | 9/2004 | Joye |
| 6,790,224 B2 | 9/2004 | Gerberding |
| 6,796,960 B2 | 9/2004 | Cioanta et al. |
| 6,805,898 B1 | 10/2004 | Wu |
| 6,811,550 B2 | 11/2004 | Holland |
| 6,838,493 B2 | 1/2005 | Williams |
| 6,858,644 B2 | 2/2005 | Benigni et al. |
| 6,863,861 B1 | 3/2005 | Zhang (Ken) |
| 6,867,247 B2 | 3/2005 | Williams |
| 6,890,339 B2 | 5/2005 | Sahatjian et al. |
| 6,890,583 B2 | 5/2005 | Chudzik et al. |
| 6,899,731 B2 | 5/2005 | Li et al. |
| 6,908,462 B2 | 6/2005 | Joye |
| 6,918,927 B2 | 7/2005 | Bates |
| 6,923,996 B2 | 8/2005 | Epstein et al. |
| 6,939,320 B2 | 9/2005 | Lennox |
| 6,942,680 B2 | 9/2005 | Grayzel |
| 6,955,661 B1 | 10/2005 | Herweck et al. |
| 6,960,346 B2 | 11/2005 | Shukla |
| 6,972,015 B2 | 12/2005 | Joye |
| 6,991,647 B2 | 1/2006 | Jadhav |
| 6,995,661 B2 | 2/2006 | Amari |
| 7,005,414 B2 | 2/2006 | Barnikol |
| 7,008,979 B2 | 3/2006 | Schottman et al. |
| 7,018,371 B2 | 3/2006 | Forman |
| 7,037,319 B2 | 5/2006 | Weber |
| 7,048,714 B2 | 5/2006 | Ritcher |
| 7,056,533 B2 | 6/2006 | Chudzik et al. |
| 7,060,051 B2 | 6/2006 | Palasis |
| 7,060,062 B2 | 6/2006 | Joye |
| 7,066,904 B2 | 6/2006 | Rosenthal et al. |
| 7,070,576 B2 | 7/2006 | Obrien |
| 7,081,112 B2 | 7/2006 | Joye |
| 7,090,655 B2 | 8/2006 | Barry |
| 7,105,175 B2 | 9/2006 | Schwarz |
| 7,108,684 B2 | 9/2006 | Farnan |
| 7,115,299 B2 | 10/2006 | Kokish |
| 7,150,738 B2 | 12/2006 | Ray |
| 7,160,317 B2 | 1/2007 | McHale |
| 7,166,098 B1 | 1/2007 | Steward et al. |
| 7,179,251 B2 | 2/2007 | Palasis |
| 7,232,486 B2 | 6/2007 | Keri |
| 7,241,455 B2 | 7/2007 | Richard |
| 7,247,338 B2 | 7/2007 | Pui |
| 7,279,002 B2 | 10/2007 | Shaw |
| 7,303,572 B2 | 12/2007 | Melsheimer |
| 7,306,625 B1 | 12/2007 | Stratford |
| 7,323,189 B2 | 1/2008 | Pathak |
| 7,335,184 B2 | 2/2008 | Laguna |
| 7,357,940 B2 | 4/2008 | Richard et al. |
| 7,364,585 B2 | 4/2008 | Weber |
| 7,371,257 B2 | 5/2008 | Sahatjian et al. |
| 7,381,418 B2 | 6/2008 | Richard |
| 7,393,685 B1 | 7/2008 | Jordan |
| 7,402,172 B2 | 7/2008 | Chin et al. |
| 7,407,671 B2 | 8/2008 | McBride et al. |
| 7,407,684 B2 | 8/2008 | Spencer et al. |
| 7,459,169 B2 | 12/2008 | Nilsson et al. |
| 7,462,165 B2 | 12/2008 | Ding et al. |
| 7,470,252 B2 | 12/2008 | Mickley et al. |
| 7,473,242 B2 | 1/2009 | Donovan et al. |
| 7,491,188 B2 | 2/2009 | Holman et al. |
| 7,494,497 B2 | 2/2009 | Weber |
| 7,527,604 B2 | 5/2009 | Naimark |
| 7,553,292 B2 | 6/2009 | Kilpatrick et al. |
| 7,572,245 B2 | 8/2009 | Herweck et al. |
| 7,588,642 B1 | 9/2009 | Morris |
| 7,604,631 B2 | 10/2009 | Reynolds |
| 7,632,288 B2 | 12/2009 | Wu |
| 7,682,387 B2 | 3/2010 | Shulze et al. |
| 7,718,213 B1 | 5/2010 | Scheer |
| 7,731,685 B2 | 6/2010 | Ragheb |
| 7,744,644 B2 | 6/2010 | Weber et al. |
| 7,750,041 B2 | 7/2010 | Speck et al. |
| 7,753,876 B2 | 7/2010 | Cervantes |
| 7,758,892 B1 | 7/2010 | Chen et al. |
| 7,762,995 B2 | 7/2010 | Eversull |
| 7,767,219 B2 | 8/2010 | Weber et al. |
| 7,771,740 B2 | 8/2010 | Strickler et al. |
| 7,773,447 B2 | 8/2010 | Kajigaya |
| 7,794,751 B2 | 9/2010 | Chudzik et al. |
| 7,803,149 B2 | 9/2010 | Bates |
| 7,811,622 B2 | 10/2010 | Bates et al. |
| 8,291,854 B2 | 10/2012 | Behnisch |
| 2001/0020151 A1 | 9/2001 | Reed et al. |
| 2002/0010489 A1 | 1/2002 | Grayzel |
| 2002/0037358 A1 | 3/2002 | Barry et al. |
| 2002/0041898 A1* | 4/2002 | Unger et al. .................. 424/486 |
| 2002/0042645 A1 | 4/2002 | Shannon |
| 2002/0151844 A1 | 10/2002 | Yang et al. |
| 2002/0183581 A1 | 12/2002 | Yoe et al. |
| 2003/0028210 A1 | 2/2003 | Boyle |
| 2003/0040712 A1 | 2/2003 | Ray et al. |
| 2003/0060877 A1 | 3/2003 | Falotico |
| 2003/0064965 A1 | 4/2003 | Ritcher |
| 2003/0077253 A1 | 4/2003 | Palasis |
| 2003/0083740 A1 | 5/2003 | Pathak |
| 2003/0114791 A1 | 6/2003 | Rosenthal et al. |
| 2003/0153870 A1 | 8/2003 | Meyer |
| 2003/0158517 A1 | 8/2003 | Kokish |
| 2003/0233068 A1 | 12/2003 | Jayaraman |
| 2003/0236513 A1 | 12/2003 | Schwarz et al. |
| 2003/0236514 A1 | 12/2003 | Schwarz |
| 2004/0023851 A1 | 2/2004 | Barnikol |
| 2004/0033251 A1 | 2/2004 | Sparer et al. |
| 2004/0034336 A1 | 2/2004 | Scott et al. |
| 2004/0039437 A1 | 2/2004 | Sparer et al. |
| 2004/0044308 A1 | 3/2004 | Naimark et al. |
| 2004/0044404 A1 | 3/2004 | Stucke et al. |
| 2004/0047911 A1 | 3/2004 | Lyu et al. |
| 2004/0059290 A1 | 3/2004 | Palasis |
| 2004/0064093 A1 | 4/2004 | Hektner et al. |
| 2004/0073284 A1 | 4/2004 | Bates et al. |
| 2004/0077948 A1 | 4/2004 | Violante et al. |
| 2004/0086569 A1 | 5/2004 | Sparer et al. |
| 2004/0098014 A1 | 5/2004 | Flugelman et al. |
| 2004/0098108 A1 | 5/2004 | Harder |
| 2004/0111144 A1 | 6/2004 | Lawin |
| 2004/0115273 A1 | 6/2004 | Sparer et al. |
| 2004/0117222 A1 | 6/2004 | Rokosz |
| 2004/0127978 A1 | 7/2004 | Sparer et al. |
| 2004/0137066 A1 | 7/2004 | Jayaraman |
| 2004/0142011 A1 | 7/2004 | Nilsson et al. |
| 2004/0143287 A1 | 7/2004 | Konstantino |
| 2004/0175406 A1 | 9/2004 | Schwarz |
| 2004/0180039 A1 | 9/2004 | Toner et al. |
| 2004/0202691 A1 | 10/2004 | Richard |
| 2004/0210191 A1 | 10/2004 | Farnan |
| 2004/0215169 A1 | 10/2004 | Li |
| 2004/0219214 A1 | 11/2004 | Gravett et al. |
| 2004/0224003 A1 | 11/2004 | Schultz |
| 2004/0224080 A1 | 11/2004 | Epstein et al. |
| 2004/0230176 A1 | 11/2004 | Shanahan et al. |
| 2004/0234575 A1 | 11/2004 | Horres |
| 2004/0260239 A1 | 12/2004 | Kusleika |
| 2005/0015046 A1 | 1/2005 | Weber et al. |
| 2005/0025801 A1 | 2/2005 | Richard et al. |
| 2005/0025802 A1 | 2/2005 | Richard et al. |
| 2005/0025803 A1 | 2/2005 | Richard et al. |
| 2005/0025848 A1 | 2/2005 | Huang |
| 2005/0027283 A1 | 2/2005 | Richard et al. |
| 2005/0037048 A1 | 2/2005 | Song |
| 2005/0037050 A1 | 2/2005 | Weber |
| 2005/0043678 A1 | 2/2005 | Freyman |
| 2005/0055077 A1 | 3/2005 | Marco et al. |

(56) References Cited

U.S. PATENT DOCUMENTS

| | | |
|---|---|---|
| 2005/0060028 A1 | 3/2005 | Horres |
| 2005/0064005 A1 | 3/2005 | Dinh et al. |
| 2005/0064038 A1 | 3/2005 | Dinh et al. |
| 2005/0095267 A1* | 5/2005 | Campbell ............... A61F 2/82 424/425 |
| 2005/0101522 A1 | 5/2005 | Speck et al. |
| 2005/0106206 A1 | 5/2005 | Herweck et al. |
| 2005/0129727 A1 | 6/2005 | Weber et al. |
| 2005/0129731 A1 | 6/2005 | Horres |
| 2005/0137618 A1 | 6/2005 | Kunis |
| 2005/0154416 A1 | 7/2005 | Herweck et al. |
| 2005/0158359 A1 | 7/2005 | Epstein et al. |
| 2005/0159704 A1* | 7/2005 | Scott ............... A61M 29/02 604/103.02 |
| 2005/0169969 A1 | 8/2005 | Li et al. |
| 2005/0176678 A1 | 8/2005 | Horres |
| 2005/0181015 A1 | 8/2005 | Zhong |
| 2005/0182361 A1 | 8/2005 | Lennox |
| 2005/0209548 A1 | 9/2005 | Dev |
| 2005/0215722 A1 | 9/2005 | Pinchunk et al. |
| 2005/0220853 A1 | 10/2005 | Dao et al. |
| 2005/0222677 A1 | 10/2005 | Bates et al. |
| 2005/0226991 A1 | 10/2005 | Hossainy et al. |
| 2005/0244456 A1 | 11/2005 | Nilsson et al. |
| 2005/0244459 A1 | 11/2005 | DeWitt et al. |
| 2005/0246009 A1 | 11/2005 | Toner et al. |
| 2005/0251106 A1 | 11/2005 | Cervantes |
| 2005/0273049 A1 | 12/2005 | Krulevitch |
| 2005/0273075 A1 | 12/2005 | Krulevitch |
| 2005/0278021 A1 | 12/2005 | Bates et al. |
| 2005/0288629 A1 | 12/2005 | Kunis |
| 2006/0002968 A1 | 1/2006 | Stewart |
| 2006/0002973 A1 | 1/2006 | Barry |
| 2006/0013853 A1 | 1/2006 | Richard |
| 2006/0013854 A1 | 1/2006 | Strickler et al. |
| 2006/0020243 A1 | 1/2006 | Speck et al. |
| 2006/0020331 A1 | 1/2006 | Bates et al. |
| 2006/0025848 A1 | 2/2006 | Weber et al. |
| 2006/0041225 A1 | 2/2006 | Wallace |
| 2006/0057208 A1 | 3/2006 | Holzer et al. |
| 2006/0058815 A1 | 3/2006 | Mickley et al. |
| 2006/0067977 A1 | 3/2006 | Labrecque |
| 2006/0079836 A1 | 4/2006 | Holman et al. |
| 2006/0083768 A1 | 4/2006 | Labrecque et al. |
| 2006/0085058 A1 | 4/2006 | Rosenthal et al. |
| 2006/0088566 A1 | 4/2006 | Parsonage |
| 2006/0088596 A1 | 4/2006 | Labrecque |
| 2006/0112536 A1 | 6/2006 | Herweck et al. |
| 2006/0121081 A1 | 6/2006 | Labrecque et al. |
| 2006/0121088 A1* | 6/2006 | Hunter et al. ............... 424/426 |
| 2006/0129093 A1 | 6/2006 | Jackson |
| 2006/0134160 A1 | 6/2006 | Troczynski et al. |
| 2006/0134168 A1 | 6/2006 | Chappa et al. |
| 2006/0135548 A1 | 6/2006 | Keri |
| 2006/0147491 A1 | 7/2006 | DeWitt et al. |
| 2006/0165754 A1 | 7/2006 | Ranade |
| 2006/0167407 A1 | 7/2006 | Weber et al. |
| 2006/0171982 A1* | 8/2006 | Timm ............... 424/422 |
| 2006/0171984 A1 | 8/2006 | Cromack et al. |
| 2006/0171985 A1 | 8/2006 | Richard et al. |
| 2006/0184112 A1 | 8/2006 | Horn |
| 2006/0188543 A1* | 8/2006 | Feng ............... 424/423 |
| 2006/0190022 A1 | 8/2006 | Beyar et al. |
| 2006/0193890 A1 | 8/2006 | Owens |
| 2006/0193891 A1 | 8/2006 | Richard |
| 2006/0195176 A1 | 8/2006 | Bates et al. |
| 2006/0200048 A1 | 9/2006 | Furst |
| 2006/0200556 A1 | 9/2006 | Brave |
| 2006/0204537 A1 | 9/2006 | Ratner et al. |
| 2006/0212106 A1 | 9/2006 | Weber et al. |
| 2006/0224115 A1 | 10/2006 | Willard |
| 2006/0228452 A1 | 10/2006 | Cromack et al. |
| 2006/0240070 A1 | 10/2006 | Cromack et al. |
| 2006/0280858 A1 | 12/2006 | Kokish |
| 2006/0286071 A1 | 12/2006 | Epstein et al. |
| 2006/0286141 A1 | 12/2006 | Campbell |
| 2007/0003599 A1 | 1/2007 | Schwarz |
| 2007/0020307 A1 | 1/2007 | Zhong et al. |
| 2007/0027523 A1 | 2/2007 | Toner et al. |
| 2007/0067882 A1 | 3/2007 | Atanasoska et al. |
| 2007/0078413 A1 | 4/2007 | Stenzel |
| 2007/0083149 A1 | 4/2007 | Steward et al. |
| 2007/0088246 A1 | 4/2007 | Steward et al. |
| 2007/0088255 A1 | 4/2007 | Toner et al. |
| 2007/0093745 A1 | 4/2007 | Steward et al. |
| 2007/0104766 A1 | 5/2007 | Wang |
| 2007/0106250 A1 | 5/2007 | Seward et al. |
| 2007/0106363 A1 | 5/2007 | Weber |
| 2007/0112330 A1 | 5/2007 | Palasis |
| 2007/0129474 A1 | 6/2007 | Salamone |
| 2007/0129792 A1 | 6/2007 | Picart et al. |
| 2007/0150465 A1 | 6/2007 | Brave |
| 2007/0150466 A1 | 6/2007 | Brave |
| 2007/0150470 A1 | 6/2007 | Brave |
| 2007/0150515 A1 | 6/2007 | Brave |
| 2007/0150646 A1 | 6/2007 | Yoon |
| 2007/0154554 A1* | 7/2007 | Burgermeister et al. ..... 424/486 |
| 2007/0178136 A1 | 8/2007 | Arney |
| 2007/0185561 A1 | 8/2007 | Schmitz |
| 2007/0202150 A1* | 8/2007 | Dave ............... A61L 31/141 424/426 |
| 2007/0212386 A1 | 9/2007 | Patravale et al. |
| 2007/0212387 A1 | 9/2007 | Patravale et al. |
| 2007/0212393 A1 | 9/2007 | Patravale et al. |
| 2007/0212394 A1* | 9/2007 | Reyes ............... A61F 2/91 424/423 |
| 2007/0224234 A1 | 9/2007 | Steckel et al. |
| 2007/0225800 A1 | 9/2007 | Sahatjian et al. |
| 2007/0232996 A1 | 10/2007 | Anderson |
| 2007/0244548 A1 | 10/2007 | Myers et al. |
| 2007/0244549 A1 | 10/2007 | Pathak |
| 2007/0254010 A1 | 11/2007 | Richard |
| 2007/0255206 A1 | 11/2007 | Reneker |
| 2007/0292478 A1 | 12/2007 | Youri |
| 2007/0299518 A1* | 12/2007 | Ruane ............... A61L 27/34 623/11.11 |
| 2008/0020013 A1 | 1/2008 | Reyes et al. |
| 2008/0021385 A1 | 1/2008 | Barry et al. |
| 2008/0027421 A1 | 1/2008 | Vancelette |
| 2008/0040314 A1 | 2/2008 | Brave |
| 2008/0050415 A1 | 2/2008 | Atanasoska et al. |
| 2008/0051541 A1 | 2/2008 | Strickler et al. |
| 2008/0057102 A1 | 3/2008 | Roorda |
| 2008/0071350 A1 | 3/2008 | Stinson |
| 2008/0071358 A1 | 3/2008 | Weber |
| 2008/0089958 A1 | 4/2008 | Diehl |
| 2008/0091008 A1 | 4/2008 | Viswanath |
| 2008/0095847 A1 | 4/2008 | Glauser et al. |
| 2008/0102033 A1 | 5/2008 | Speck et al. |
| 2008/0102034 A1 | 5/2008 | Speck et al. |
| 2008/0104004 A1 | 5/2008 | Brave |
| 2008/0113081 A1 | 5/2008 | Hossainy et al. |
| 2008/0118544 A1 | 5/2008 | Wang |
| 2008/0132992 A1 | 6/2008 | Bates et al. |
| 2008/0140002 A1 | 6/2008 | Ramzipoor et al. |
| 2008/0145396 A1 | 6/2008 | Bates et al. |
| 2008/0145398 A1 | 6/2008 | Bates et al. |
| 2008/0157444 A1 | 7/2008 | Melsheimer |
| 2008/0171129 A1 | 7/2008 | Ranade et al. |
| 2008/0175887 A1 | 7/2008 | Wang |
| 2008/0195042 A1 | 8/2008 | Weber |
| 2008/0195079 A1 | 8/2008 | Moore et al. |
| 2008/0199506 A1 | 8/2008 | Horres |
| 2008/0206304 A1 | 8/2008 | Lindquist et al. |
| 2008/0208182 A1 | 8/2008 | Lafontaine |
| 2008/0220041 A1 | 9/2008 | Brito et al. |
| 2008/0249464 A1 | 10/2008 | Spencer et al. |
| 2008/0255508 A1 | 10/2008 | Wang |
| 2008/0255509 A1 | 10/2008 | Wang |
| 2008/0255510 A1 | 10/2008 | Wang |
| 2008/0274159 A1 | 11/2008 | Schultz |
| 2008/0276935 A1 | 11/2008 | Wang |
| 2008/0287984 A1 | 11/2008 | Weber et al. |
| 2008/0311173 A1 | 12/2008 | Schwarz et al. |

(56) References Cited

U.S. PATENT DOCUMENTS

| | | |
|---|---|---|
| 2009/0005849 A1 | 1/2009 | Hossainy et al. |
| 2009/0018501 A1 | 1/2009 | Yribarren et al. |
| 2009/0024200 A1 | 1/2009 | Wilcox et al. |
| 2009/0047414 A1 | 2/2009 | Corbeil et al. |
| 2009/0048667 A1 | 2/2009 | Mochizuki |
| 2009/0054837 A1 | 2/2009 | Won Hoist et al. |
| 2009/0069883 A1 | 3/2009 | Ding et al. |
| 2009/0076448 A1 | 3/2009 | Consigny et al. |
| 2009/0088735 A1 | 4/2009 | Abboud |
| 2009/0098176 A1 | 4/2009 | Helmus |
| 2009/0105686 A1 | 4/2009 | Snow et al. |
| 2009/0105687 A1 | 4/2009 | Deckman et al. |
| 2009/0111960 A1 | 4/2009 | Parsonage |
| 2009/0112239 A1 | 4/2009 | To |
| 2009/0120361 A1 | 5/2009 | Schiele |
| 2009/0136560 A1 | 5/2009 | Bates et al. |
| 2009/0187144 A1 | 7/2009 | Jayaraman |
| 2009/0192537 A1 | 7/2009 | Obrien |
| 2009/0204082 A1 | 8/2009 | Wesselmann et al. |
| 2009/0226502 A1 | 9/2009 | Chen |
| 2009/0227948 A1 | 9/2009 | Chen et al. |
| 2009/0227949 A1 | 9/2009 | Knapp et al. |
| 2009/0227980 A1 | 9/2009 | Kangas et al. |
| 2009/0246252 A1 | 10/2009 | Arps et al. |
| 2009/0254063 A1 | 10/2009 | Oepen et al. |
| 2009/0258049 A1 | 10/2009 | Klein et al. |
| 2009/0276036 A1 | 11/2009 | Nagura |
| 2009/0299355 A1 | 12/2009 | Bencini |
| 2009/0299356 A1 | 12/2009 | Watson |
| 2009/0318848 A1 | 12/2009 | Shippy, III et al. |
| 2010/0010470 A1 | 1/2010 | Bates |
| 2010/0015200 A1 | 1/2010 | McClain et al. |
| 2010/0023108 A1 | 1/2010 | Toner et al. |
| 2010/0030183 A1 | 2/2010 | Toner et al. |
| 2010/0036585 A1 | 2/2010 | Scharfenberg |
| 2010/0049294 A1 | 2/2010 | Zukowski et al. |
| 2010/0049296 A1 | 2/2010 | Sarasam et al. |
| 2010/0049309 A1 | 2/2010 | Bates et al. |
| 2010/0055294 A1 | 3/2010 | Wang et al. |
| 2010/0056985 A1 | 3/2010 | Weber et al. |
| 2010/0063585 A1 | 3/2010 | Hoffmann et al. |
| 2010/0069838 A1 | 3/2010 | Weber |
| 2010/0074934 A1 | 3/2010 | Hunter |
| 2010/0076542 A1 | 3/2010 | Orlowski |
| 2010/0087783 A1 | 4/2010 | Weber et al. |
| 2010/0092540 A1 | 4/2010 | Pinchuk et al. |
| 2010/0096781 A1 | 4/2010 | Huang et al. |
| 2010/0125239 A1 | 5/2010 | Perry et al. |
| 2010/0131043 A1 | 5/2010 | Casas et al. |
| 2010/0145266 A1 | 6/2010 | Orlowski |
| 2010/0179475 A1 | 7/2010 | Hoffmann et al. |
| 2010/0198190 A1 | 8/2010 | Michal et al. |
| 2010/0209471 A1 | 8/2010 | Weber |
| 2010/0209473 A1 | 8/2010 | Dhont et al. |
| 2010/0228333 A1 | 9/2010 | Drasler et al. |
| 2010/0233228 A1 | 9/2010 | Speck |
| 2010/0233236 A1 | 9/2010 | Zhao |
| 2010/0239635 A1 | 9/2010 | McClain et al. |
| 2010/0249702 A1 | 9/2010 | Magana et al. |
| 2010/0256748 A1 | 10/2010 | Taylor |
| 2010/0261662 A1 | 10/2010 | Schreck et al. |
| 2010/0268191 A1 | 10/2010 | Trudel et al. |
| 2010/0272773 A1 | 10/2010 | Kangas et al. |
| 2010/0272778 A1 | 10/2010 | McClain |
| 2010/0285085 A1 | 11/2010 | Stankus et al. |
| 2010/0292641 A1 | 11/2010 | Wijay et al. |
| 2010/0298769 A1 | 11/2010 | Schewe et al. |
| 2010/0312182 A1 | 12/2010 | Adden et al. |
| 2010/0318020 A1 | 12/2010 | Atanasoska et al. |
| 2010/0324645 A1 | 12/2010 | Stankus et al. |
| 2010/0324648 A1 | 12/2010 | Scheller et al. |
| 2010/0331816 A1 | 12/2010 | Dadino et al. |
| 2010/0331947 A1 | 12/2010 | Shalev et al. |
| 2011/0008260 A1 | 1/2011 | Flanagan |
| 2011/0015664 A1 | 1/2011 | Kangas |
| 2011/0020151 A1 | 1/2011 | Tiefenthaler |
| 2011/0054396 A1 | 3/2011 | Kangas et al. |
| 2011/0054443 A1 | 3/2011 | Weber |
| 2011/0087191 A1 | 4/2011 | Scheuermann |
| 2011/0152765 A1 | 6/2011 | Weber |
| 2011/0160645 A1 | 6/2011 | Sutermeister |
| 2011/0160659 A1 | 6/2011 | Clarke |
| 2011/0160698 A1 | 6/2011 | Hoffmann |
| 2011/0178503 A1 | 7/2011 | Kangas |
| 2011/0196340 A1 | 8/2011 | Barry |
| 2011/0251590 A1 | 10/2011 | Weber |
| 2011/0270152 A1 | 11/2011 | Atanasoska |
| 2011/0275980 A1 | 11/2011 | Weber |
| 2011/0301565 A1 | 12/2011 | Weber |
| 2012/0095396 A1 | 4/2012 | Radhakrishnan |
| 2012/0231037 A1 | 9/2012 | Levi |
| 2013/0035483 A1 | 2/2013 | Zeng |
| 2013/0053947 A1 | 2/2013 | Kangas |

FOREIGN PATENT DOCUMENTS

| | | |
|---|---|---|
| DE | 102004020856 | 4/2005 |
| EP | 0383429 | 1/1990 |
| EP | 0372088 | 6/1990 |
| EP | 0379156 | 7/1990 |
| EP | 0399712 | 11/1990 |
| EP | 0470246 | 2/1991 |
| EP | 0551182 | 7/1993 |
| EP | 0568310 | 11/1993 |
| EP | 0577215 A1 | 1/1994 |
| EP | 0734721 | 3/1996 |
| EP | 0747069 | 4/1996 |
| EP | 0519063 | 5/1996 |
| EP | 0712615 | 5/1996 |
| EP | 0717041 | 6/1996 |
| EP | 0770401 | 5/1997 |
| EP | 0633796 | 11/1997 |
| EP | 0937469 | 8/1999 |
| EP | 0950386 | 10/1999 |
| EP | 0623354 | 10/2002 |
| EP | 1189553 | 3/2004 |
| EP | 1407726 | 4/2004 |
| EP | 1521603 | 4/2005 |
| EP | 1667760 | 6/2006 |
| EP | 1372737 | 12/2006 |
| EP | 1810665 | 7/2007 |
| EP | 1810665 A1 | 7/2007 |
| EP | 1666071 | 8/2007 |
| EP | 1666070 | 9/2007 |
| EP | 1857127 | 11/2007 |
| EP | 1868663 A2 | 12/2007 |
| EP | 1539266 | 4/2008 |
| EP | 1981559 | 10/2008 |
| EP | 1996246 | 12/2008 |
| EP | 2043704 | 4/2009 |
| EP | 2108390 | 10/2009 |
| EP | 2125058 | 12/2009 |
| EP | 2125060 | 12/2009 |
| EP | 1594459 | 2/2010 |
| EP | 1669092 | 3/2010 |
| EP | 2172242 | 4/2010 |
| EP | 1534356 | 7/2010 |
| EP | 1786487 | 11/2010 |
| EP | 2251050 | 11/2010 |
| EP | 2241341 | 1/2011 |
| EP | 2944332 A1 | 11/2015 |
| GB | 2112646 | 7/1983 |
| GB | 2127839 | 9/1983 |
| JP | 663145 | 3/1994 |
| JP | 663145 A | 3/1994 |
| JP | 2002240847 | 8/2002 |
| RU | 200513564 | 4/2004 |
| WO | 1989012478 | 12/1989 |
| WO | 1991008790 | 6/1991 |
| WO | 1992011896 | 7/1992 |
| WO | 1992015286 | 9/1992 |
| WO | 1993006792 | 4/1993 |
| WO | 94/18954 A1 | 9/1994 |
| WO | 1994021308 | 9/1994 |

(56) References Cited

FOREIGN PATENT DOCUMENTS

| | | |
|---|---|---|
| WO | 1994023787 | 10/1994 |
| WO | 9503036 | 2/1995 |
| WO | 9503083 | 2/1995 |
| WO | 1995003036 | 2/1995 |
| WO | 1995008305 | 3/1995 |
| WO | 1995021636 | 8/1995 |
| WO | 1996025176 | 8/1996 |
| WO | 1996032907 | 10/1996 |
| WO | 9639949 | 12/1996 |
| WO | 1997010011 | 3/1997 |
| WO | 1997025085 | 7/1997 |
| WO | 9733552 | 9/1997 |
| WO | 9741916 | 11/1997 |
| WO | 97/45105 A1 | 12/1997 |
| WO | 1998031415 | 7/1998 |
| WO | 9901458 | 1/1999 |
| WO | 9908729 | 2/1999 |
| WO | 1999008729 | 2/1999 |
| WO | 99/16500 | 4/1999 |
| WO | 99/25336 | 5/1999 |
| WO | 1999029353 | 6/1999 |
| WO | 00/32267 | 6/2000 |
| WO | 0032238 | 6/2000 |
| WO | 2000032238 | 6/2000 |
| WO | 00/45744 | 8/2000 |
| WO | 0149358 | 7/2001 |
| WO | 0160441 | 8/2001 |
| WO | 0238065 | 5/2002 |
| WO | 2002043796 | 6/2002 |
| WO | 02076509 | 10/2002 |
| WO | 03022265 | 3/2003 |
| WO | 2003026718 | 4/2003 |
| WO | 2003059430 | 7/2003 |
| WO | 03094991 | 11/2003 |
| WO | 2004028582 | 4/2004 |
| WO | 2004028610 | 4/2004 |
| WO | 2004050140 | 6/2004 |
| WO | 2004060346 | 7/2004 |
| WO | 2004060471 | 7/2004 |
| WO | 2004089958 | 10/2004 |
| WO | 2004091684 | 10/2004 |
| WO | 2005027994 | 3/2005 |
| WO | 2005027996 | 3/2005 |
| WO | 2005032611 | 4/2005 |
| WO | 2006036970 | 4/2006 |
| WO | 2006039237 | 4/2006 |
| WO | 2006/063021 A2 | 6/2006 |
| WO | 2006/102359 | 9/2006 |
| WO | 2006102359 A2 | 9/2006 |
| WO | 2006108420 | 10/2006 |
| WO | 2006116348 | 11/2006 |
| WO | 2006116989 | 11/2006 |
| WO | 2006130326 | 12/2006 |
| WO | 2007011707 | 1/2007 |
| WO | 2007/030512 A2 | 3/2007 |
| WO | 2007090382 | 8/2007 |
| WO | 2007090385 | 8/2007 |
| WO | 2008/003298 | 1/2008 |
| WO | 2008014222 | 1/2008 |
| WO | 2008045228 | 4/2008 |
| WO | 2008/086794 | 7/2008 |
| WO | 2008/089730 | 7/2008 |
| WO | 2008/089730 A2 | 7/2008 |
| WO | 2008086794 | 7/2008 |
| WO | 2008101486 | 8/2008 |
| WO | 2007109114 | 9/2008 |
| WO | 2008109114 | 9/2008 |
| WO | 2008/125890 | 10/2008 |
| WO | 2008/137237 | 11/2008 |
| WO | 2009002855 | 12/2008 |
| WO | 2009014692 | 1/2009 |
| WO | 2009018816 | 2/2009 |
| WO | 2009018816 A2 | 2/2009 |
| WO | 2009/036118 | 3/2009 |
| WO | 2009026914 | 3/2009 |
| WO | 2009036135 | 3/2009 |
| WO | 2009/066330 | 5/2009 |
| WO | 2009096822 | 8/2009 |
| WO | 2009100394 | 8/2009 |
| WO | 2009120361 | 10/2009 |
| WO | 2009121565 | 10/2009 |
| WO | 2009/135125 | 11/2009 |
| WO | 2010009335 | 1/2010 |
| WO | 2010/021757 | 2/2010 |
| WO | 2010026578 | 3/2010 |
| WO | 2010079218 | 7/2010 |
| WO | 2010080575 | 7/2010 |
| WO | 2010086863 | 8/2010 |
| WO | 2010096476 | 8/2010 |
| WO | 2010111232 | 9/2010 |
| WO | 2010120620 | 10/2010 |
| WO | 2010124098 | 10/2010 |
| WO | 2010146096 | 12/2010 |
| WO | 2010147805 | 12/2010 |
| WO | 2011/005421 A9 | 1/2011 |
| WO | 2011009096 | 1/2011 |
| WO | 2011028419 | 3/2011 |
| WO | 2011097103 | 8/2011 |

OTHER PUBLICATIONS

Abstract from Liggins, R. T., Hunter, W. L and Burt, H. M. 'Solid-state characterization of paclitaxel.' Journal of Pharmaceutical Sciences, 86: 1458-1463, (1997).

Abstracts from the 70th Scientific Sessions, Orange County Convention center, Orlando, Florida, Nov. 9-12, 1997, Supplement to Circulation, vol. 96, No. 8, Supplement I, 1-341,1-288 and 1-608.

Alexis et al., 'In vitro study of release mechanisms of paclitaxel and rapamycin from drug-incorporated biodegradable stent matrices' Journal of Controlled Release 98 (2004) 67-74.

Axel, Dorothea I., et al., Paclitaxel Inhibits Arterial Smooth Muscle Cell Proliferation and Migration In Vitro and In Vivo Using Local Drug Delivery, Jul. 15, 1997, vol. 96 (2), 636-651.

Axel De Labriolle et al., "Paclitaxel-eluting balloon: From bench to bed", Catheterization and Cardiovascular Interventions, vol. 73. No. 5, Apr. 1, 2009, pp. 643-652.

Buvardi, S., et al., 'Merck Index', 1996, Merck and Co., p. 144.

Cardiovascular and Interventional Radiology, Supplement 1, Sep. 28-Oct. 2, 1997, 158-161.

Consigny PM, Barry JJ, Vitali NJ.; 'Local Delivery of an Antiproliferative Drug with Use of Hydrogel-coated Angioplasty Balloons1' J Vasc Intery Radiol. Jul.-Aug. 1994;5(4):553-60.

Cortese et al., "Paclitaxel-coated balloon versus drug-eluting stent during PCI of small coronary vessels, a prospective randomised clinical trial. The PICCOLETO Study", Heart 2010; 96:1291-1296.

Finkelstein et al., "Local Drug Delivery via a Coronary Stent with Programmable Release Pharmocokinetics," 2003, Circulation, 107, 777-784.

International Preliminary Report on Patentability of International Application No. PCT/DE20071001173 dated Aug. 4, 2009.

J. Wohrle et al., 'Comparison of the heparin coated vs the uncoated Jostent no influence on restenosis or clinical outcome' European Heart Journal, 2001, vol. 22, pp. 1808-1816.

Partial European Search Report in EP 07005256.8, dated Jan. 25, 2008.

PCT/US 08/72660 Search Report, dated Nov. 6, 2008.

PCT/US 2005/47235 Search Report, dated Dec. 28, 2005.

Presentation by Dr. Cortese, "Paclitaxel-eluting balloon versus paclitaxel-eluting stent in small coronary vessel disease." The Piccoleto Trial.

Scheller et al., "Treatment of Coronary In-Stent Restenosis with a Paclitaxel-Coated Balloon Catheter", The New England Journal of Medicine, 2006; 355:2113-24.

Scollott, S.J., et al., Taxol Inhibits Neointimal Smooth Muscle Cell Accumulation after Angioplasty in the Rat, 1995, Journal of Clinical Investigation, 95, pp. 1869-1876.

Westedt et al., "Paclitaxel releasing films consisting of poly(vinyl alcohol)-graft-poly(lactide-co-glycolide) and their potential as biodegradable stent coatings." 2006, J Control Release 111, 235-46 (abstract).

(56) References Cited

OTHER PUBLICATIONS

Written Opinion for PCT/DE2008/000096.
Xu et al., "Lactic-co-glycolic acid polymer with rapamycin coated stent reduces neo-intimal formation in a porcine coronary model", Journal of Clinical Cardiology, 2004, abstract.
Dowding et al., "Preparation and Swelling Properties of Poly(NIPAM) "Minigel" Particles Prepared by Inverse Suspension Polymerization," Journal of Colloid and Interface Science 221, 268-272 (2000).
Panda et al., "Synthesis and swelling characteristics of poly(N-isopropylacrylamide) temperature sensitive hydrogels crosslinked by electron beam irradiation," Radiation Physics and Chemistry 58 (2000) 101-110.
U.S. Appl. No. 61/394,104, filed Oct. 18, 2010; Inventor: Radhakrishnan et al.
Scheller et al., "A further alternative; Balloons can be coated, as well" Newsletter from annual meeting in DGK Apr. 21, 2006.
Mondesire (Targeting Mammalian Target of Rapamycin Synergistically Enhances Chemotherapy-Induced Cytotoxicity in Breast Cancer Cells, 10 Clin. Cancer Res. 7031 (2004).
U.S. Appl. No. 61/271,167, filed Jul. 17, 2009.
U.S. Appl. No. 61/527,203, filed Aug. 25, 2011.
U.S. Appl. No. 13/242,445, filed Sep. 23, 2011, Kangas et al.
PCT Search Report and Written Opinion for PCT/US2010/038534, dated May 11, 2011.
Sigma-Aldrich, "Paclitaxel" Product Information, date unknown. Documents indicates Jun. 2009 in lower corner. Applicant does not know if this is a date.
Certified Priority Document U.S. Appl. No. 61/224,723, filed Jul. 10, 2009, entitled "Use of nanocrystals for drug delivery from a balloon", Aiden Flanagan et al.
Hancock, Bruno et al., "Characteristics and Significance of the Amorphous State in Pharmaceutical Systems", Journal of Pharmaceutical Science, 86(1):1-12, Jan. 1997.
Gebrauchsinfomration: Information für den Anwender zu Ultravist-300®, 10 pages, Feb. 2017.
Paclitaxel, Wikipediaeintrag, der freien Enzyklopädie, 3 pages, May 18, 2009.
Merisko-Liverside, E. et al., "Formulation and Antitumor Activity Evaluation of Nanocrystalline Suspensions of Poorly Soluble Anticancer Drugs", Pharmaceutical Research, 13(2): 272-278, 1996.
Voigt, Rudolf, Pharmazeutische Technologie, 8th Ed., 3 pgs., Ullstein Mosby, 1995.
Zimmermann, Ingfried, Pharmazeutische Technologie, Springer, 3 pgs., 1998.
Bauer, Kurt H. et al., Pharmazeutische Technologie, 4th Ed., pp. 286-287, Thieme, 1993.
Etzler, Frank M., et al., "Particle Size Analysis: a Comparative Study of Various Methods", Part. Part. Syst. Charact. 12:217-224, 1995.
Brittain, Harry G., "What is the "Correct" Method to Use for Particle-Size Determination?", Pharmaceutical Technology, p. 96-98, Jul. 2001.
Safety Data Sheet of Sigma Aldrich for Tributyl O-acetylcitrate, 7 pgs., 2015.
Product Information of Sigma-Aldrich, Inc., about Paclitaxel, sigma-aldrich.com, 3 pgs., 2009.
Liggins, Richard T., et al., "Solid-State Characterization of Paclitaxel", Journal of Pharmaceutical Sciences, 86(12): 1458-1463, Dec. 1997.
Acker, Andrea, et al., "Lexikon der Chemie", Spektrum Akademischer Verlag, 3:89-91, 1999.
Jakubke, H.-D., et al., "Concise Encyclopedia of Biochemistry", Walter de Gruyter, p. 162-163, 1983.
Scheller, Bruno, et al., "Treatment of Coronary In-Stent Restenosis with a Paclitaxel-Coated Balloon Catheter", New Engl. J. Med., 355:2113-2124, Nov. 16, 2006.
Rao, Koppakva V., et al. "A Large Scale Process for Paclitaxel and other Taxanes from the Needles of Taxus x media hicksii and Taxus floridana Using Reverse Phase Column Chromatography", J. Liq. Chrom. & Rel. Technol., 19(3):427-447, 1996.
Rao, Koppakva V., et al., "Taxanes from the Bark of Taxus brevifolia", Phytochmistry, 41(3):863-866, 1996.
Annex: Decision T 1857/07 of Board of Appeals of the EPO, Jul. 9, 2010.
Junghanns, Jens-Uwe A H, et al., "Nanocrystal technology, drug deliver and clinical applications", International Journal of Nanomedicine, 3(3): 295-309, 2008.
Letter from Peterreins Schley of Dec. 16, 2015 to European Patent Office, 5pgs.

* cited by examiner

USE OF NANOCRYSTALS FOR DRUG DELIVERY FROM A BALLOON

CROSS-REFERENCE TO RELATED APPLICATIONS

This application claims benefit of application from Ser. No. 61/224723 filed on Jul. 10, 2009, the contents of which is hereby incorporated by reference.

BACKGROUND OF THE INVENTION

Balloons coated with paclitaxel containing formulations are known. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

Paclitaxel coated balloons that provide high release rates from the balloon surface have recently been developed. However these balloons do not yet provide for delivery of predictable amounts of the drug to the tissue at the delivery site nor do they provide for a predictable therapeutic drug tissue level over an extended time period.

In regards to drug delivery from a balloon, currently a mixture of a drug (paclitaxel) and a secondary substance in solution is sprayed or dip-coated on a balloon surface and dried, creating a solid matrix of the two components on the balloon surface which breaks off in undefined and sometimes very large pieces upon deployment of the balloon. These pieces can be up to hundreds of micrometers. A variety of negative effects can as such be described.
 a/ The distribution of the particles over the vessel wall is non-uniform. Having large chucks at one place automatically means a void at other places.
 b/ The uptake into the tissue is different as it is known that single micrometer sized and nano-sized particles are better absorbed by cells. So, with the current matrix breaking up in a wide distribution of chunks part will be absorbed and part will hang on the wall or float downstream.
Furthermore having the drug being sprayed in solution causes the drug to be present in the final coating on the balloon surface in an unknown mixture of amorphous and crystalline nature. It is known, however, that a crystalline or amorphous morphology of paclitaxel greatly affects the extended release kinetics of the drug in tissue.

SUMMARY OF THE INVENTION

The invention addresses problems both with the morphological form of the drug and the reproducibility of the particles delivered by a drug delivery balloon. The invention uses nano-crystalline particles of a drug component to provide for a controlled morphology and particle size. According to the invention, the drug is put into a preferred size and morphology before it is applied to the balloon, and the particles are loaded onto the balloon in a manner that preserves these features during application process.

One aspect of the invention pertains to a drug delivery balloon adapted for delivery of a drug to a site in a body passageway, the balloon comprising a balloon wall with an outer surface, and the balloon having a drug disposed on the outer surface, wherein the drug is provided on the balloon as crystalline particles of said drug in a predetermined size distribution.

In some embodiments the drug is provided as a mixture at least two different narrow size distributions, selected to provide a tissue residence of the drug at the application site In some aspects the nanocrystalline drug particles are accompanied in a predetermined ratio with marker particles that allow for the monitoring of the delivery location and dosage.

Other aspects of the invention pertain to methods of increasing particle capacity of the balloons.

In another aspect the invention pertains to a drug delivery balloon comprising a coating thereon and a drug applied over the coating, wherein the coating has a textured surface that increases the drug carrying capacity of the balloon.

Still other aspects of the invention are described in the Figures, the Detailed Description of Preferred Embodiments and/or in the Claims below.

DETAILED DESCRIPTION OF PREFERRED EMBODIMENTS

As used herein the term drug delivery balloon pertains to a balloon that has an outer surface coating that carries a drug that is delivered to a tissue site when a device carrying the balloon is provided at the tissue site and the balloon is expanded. The drug coating may be part of a single or multilayered system and the drug may be accompanied by various excipient substances that facilitate retention during delivery and/or release of the drug from the balloon surface.

According to the invention a drug delivery balloon is provided as particles of said drug of a controlled size distribution. In at least some embodiments the drug particles comprise greater than 90%, for instance at least 95%, at least 98% or at least 99% of the drug.

Drug particles useful in the invention may be prepared from crystalline drug form material obtained in any suitable manner which is ground or milled to the desired size. In some instances cryogrinding, e.g. at temperatures of −40° C. or less, may be useful. Sieving or other classification techniques can be used to confine the distribution of the particles to a desired range. This allows the size distribution of the crystalline particles to be controlled precisely. In some embodiments the particles are substantially all about 1 µm or less. The particle size may be in the range of 0.01-2.0 µm (10-2000 nm). In at least some embodiments a narrower size range for instance 0.01-0.1 µm; 0.01-0.2 µm; 0.01-0.5 µm; 0.1-0.3 µm; 0.1-0.4 µm; 0.2-0.4 µm; 0.1-0.5 µm; 0.2-0.4 µm; 0.2-0.5 µm; 0.2-0.6 µm; 0.3-0.5 µm; 0.3-0.6 µm; 0.3-0.7 µm;

0.4-0.6 µm; 0.4-0.7 µm; 0.4-0.8 µm; 0.5-0.7 µm; 0.5-0.8 µm; 0.5-0.9 µm; 0.5-1.0 µm; 0.6-0.8 µm; 0.6-0.9 µm; 0.6-1.0 µm; 0.7-0.9 µm; 0.7-1.0 µm, 0.7-1.1 µm; 0.8-1.0 µm; 0.8-1.1 µm; 0.8-1.2 µm; 0.9-1.1 µm; 0.9-1.3 µm; 1.0-1.3 µm; 1.0-1.5 µm; 1.0-2.0 µm; 1.5-2.0 µm, is employed. By providing the drug in a specific particle size range the dosage at the tissue site will be more predictable than is currently provided from drug delivery balloons.

Multi-modal ranges, prepared, e.g by mixing two or more sets of different narrow size range may be used in some cases to provide a desired bioavailability profile over time. For example 50% of the crystals can be of 1000 nm mean size and the other 50% could be 300 nm mean size. This embodiment enables a tailoring of the drug persistence in the vessel wall. The smaller crystals will more readily dissolve and enter the tissue for immediate effect and larger crystals will dissolve at a much slower rate enabling longer drug persistence.

In at least some embodiments the drug particles are not microcapsules (i.e. the drug particle does not include an encapsulant enclosing the drug). However, it is contemplated that the drug particles may be carried in an excipient layer and that the drug particles may comprise minor amount of additives that stabilize the particles against agglomeration by surface adsorption of selected stabilizers. Suitable stabilizers may be a GRAS (Generally Regarded As Safe) stabilizer, e.g. a GRAS surfactant, anti-block agent or the like. Such GRAS stabilizers are desirably employed in concentrations of less than 1% by weight of the drug particle and are typically applied after the particles have been milled to size.

The prepared particles remain intact as they are applied to the balloon. That is, they are not dissolved or melted during application. However, the particles may be dispersed in a liquid, e.g. aqueous, medium that also includes a excipient material. The excipient may be polymer, a contrast agent, a surface active agent, or other small molecule. The drug suitably will be is substantially insoluble in the excipient. In some embodiments the drug particle is formulated with an excipient. An excipient is an additive to a drug-containing layer that facilitates adhesion to the balloon and/or release from the balloon upon expansion. Suitably the excipient is a material that is very readily soluble in body fluids and in which the drug is not soluble.

In some embodiments the excipient may remain on the delivery device at the time of drug transfer but allow efficient transfer of the drug from the mixture. In some embodiments the excipient provides weak phase boundaries with the drug particles that are easily overcome when a balloon is expanded, regardless of whether the excipient remains on the device or initially leaves the device with the drug. In some embodiments the excipient substantially degrades or dissolves in the course of the deployment or during transfer of the drug from the device at the site of administration such that little or none of the excipient is detectable on the tissue after a short interval, for instance an interval of 2 days, 1 day, 12 hours, 4 hours, 1 hour, 30 minutes, 10 minutes or 1 minute. In some embodiments dissolution or degradation of the excipient during deployment provides porosities in the drug-containing layer by the time the device is at the site of administration.

Examples of excipient materials that may be used include sugars (e.g., mannitol), polysaccharides (e.g. heparin), citrate esters (e.g. tributyl citrate, triethyl citrate, acetyltributyl citrate and/or acetyltriethyl citrate), contrast agents (e.g. iopamide), water soluble polymers (e.g. polyvinyl pyrrolidone), pharmaceutically acceptable salts, and the like.

In some embodiments the drug containing layer is applied over an underlayer of material that has a high solubility in bodily fluids to undercut the drug facilitate breakup of the drug-containing layer upon balloon expansion. An example of a suitable underlayer material is pectin.

Numerous other excipients and additive compounds, protective polymer layers, underlayer materials and drugs are described in one or more of the following documents:

U.S. Pat. No. 5,102,402, Dror et al (Medtronic, Inc.)
U.S. Pat. No. 5,370,614, Amundson et al, (Medtronic, Inc.)
U.S. Pat. No. 5,954,706, Sahatjian (Boston Scientific Corp)
WO 00/32267, SciMed Life Systems; St Elizabeth's Medical Center (Palasis et al)
WO 00/45744, SciMed Life Systems (Yang et al) R. Charles, et al, "Ceramide-Coated Balloon Catheters Limit Neointimal Hyperplasia After Stretch Injury in Cartoid Arteries," *Circ. Res.* 2000; 87; 282-288
U.S. Pat. No. 6,306,166, Barry et al, (SciMed Life Systems, Inc.)
US 2004/0073284, Bates et al (Cook, Inc; MED Inst, Inc.)
US 2006/0020243, Speck
WO 2008/003298 Hemoteq AG, (Hoffman et al)
WO 2008/086794 Hemoteq AG, (Hoffman et al)
US 2008/0118544, Wang
US 20080255509, Wang (Lutonix)
US 20080255510, Wang (Lutonix)

All incorporated herein by reference in their entirety. In some cases paclitaxel has been applied directly to the balloon or to a coating placed on the balloon. In other cases paclitaxel has been formulated with an excipient that may be polymer, a contrast agent, a surface active agent, or other small molecules that facilitate adhesion to the balloon and/or release from the balloon upon expansion. The formulations have typically been applied from solution, and may be applied to the entire balloon or to a folded balloon, either by spraying, immersion or by pipette along the fold lines.

The drug is one that has therapeutic benefit at a site reachable by a balloon carrying medical device such as a catheter, endoscope or the like, and that is desirably provided in a therapeutic dosage that lasts for at least several hours or days. Desirably the drug has a characterizable crystalline form that provides limited solubility in aqueous body fluids. In such case the particle will have a lifetime at the site that is at least partly a function of its size, for instance a lifetime of a therapeutically effective dosage of 5 days, 10 days, 20 days, 30 days or 40 days after delivery.

According to the invention the drug is one that has a characteristic crystalline forms. In some embodiments the drug is a crystallizable, lipophilic, substantially water insoluble drug. The drugs which can be used in embodiments of the present invention, can be any therapeutic agent or substance that has therapeutic benefit for local administration by delivery from a medical device inserted into the body. Specific examples of drugs include anti-restenosis and anti-angeogenic drugs delivered in conjunction with a dilatation of a constriction or lesion in the vascular system and/or with stent placement. Specific examples of such drugs include paclitaxel, rapamycin, everolimus and mixtures thereof. In the case of mixtures the particles of the various drugs may have the same or different size distributions. For instance if a first drug has a desired therapeutic benefit shortly upon contact, and a second drug requires a desired effect over longer period the particles of the first drug may be provided a smaller size relative to those of the second drug.

Figure 1:
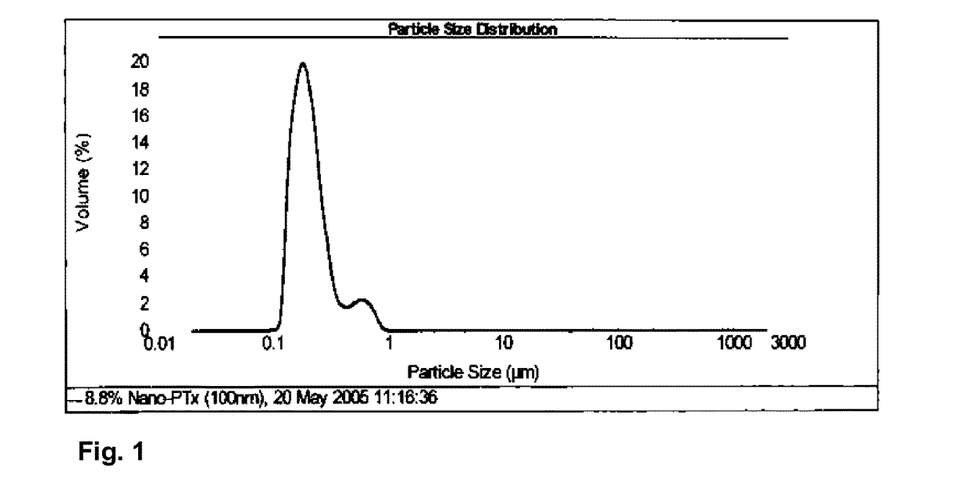
FIG. 1 Graph showing particle size distribution of exemplary paclitaxel crystalline particles.

In some embodiments of the invention the drug is paclitaxel. Nanocrystalline particles of paclitaxel dihydrate can be obtained for example from Elan Drug Technologies, Monksland, Athlone, County Westmeath, Ireland (website: http://www.elandrugtechnologies.com/nav/14/). Referring to FIG. 1, there is shown a particle size distribution profile of a specific embodiment of nanocrystalline paclitaxel dehydrate useful in an embodiment of the invention.

The drug particles are provided on the surface of the balloon. As already mentioned other components may be provided in the drug particle layer, e.g. excipient materials that bind the particles to the balloon or to each other, or various materials that provide the balloon surface with higher effective surface area so as to increase the particle retention capacity of the balloon.

The use of particles of a narrow size distribution on drug delivery balloons also allows solution of another issue that arises with drug delivery from a balloon, namely to how to allow the physician to control the amount and area of the delivered drug amount. A small amount of traceable nanoparticles, desireably of essentially the same size profile so that the distribution on the balloon and in the body is propostional, may be mixed in the suspension of the nanocrystalline drug particles. The mixed drug particle/tracer particle suspension is then sprayed onto the balloon surface and dried. Traceable particles are for example those that can be detected by MRI or X-Ray by ultrasound. With the release of the drug particles from the surface, one will have a simultaneous release of the tracer particles allowing detection of the density and placement of the drug release to the vessel wall. In case the physician determines that the coverage obtained was too low, the physician can redeploy the existing or a new balloon. This same tracer system also allows deploying a second balloon to an area close or directly adjacent to an already treated area and while avoiding overlap which if the drug has a risk of providing too high of a dose when applied in overlapping areas.

Reference is made to FIGS. 2-5 depicting various aspects of the invention. In FIG. 1 there is shown a portion 10 of a balloon surface that is covered with nanocrystalline drug particles 12 and tracer particles 14. The tracer particles may be particles detectable by any remote imaging means, for instance the particles 14 may detectable by MRI (e.g., magnetite), X-Ray (e.g. Gold) or by ultrasound (e.g. air containing urethane capsules). The tracer particles and are preferably present in a known ratio relative to the drug particles 12 so that both the location and concentration of the drug particles can be estimated.

Figure 2:
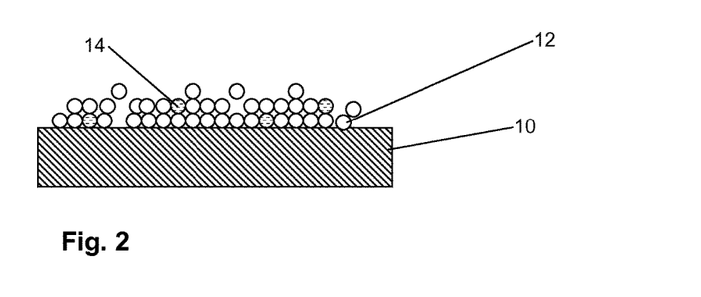
FIG. 2 Schematic depiction of a balloon surface coated with nanocrystalline drug particles and tracer particles.

FIG. 2 is similar to FIG. 1 except that a second different type of tracer particles 16 are also provided allowing detection by multiple techniques. This allows more flexibility to the physician in detection and in optimization of quantification. Of, course it is also possible to include even more than two different types of detectable particles without departing from the invention.

In some embodiments the drug particles are suspended in an aqueous media, that may optionally also contain dissolved matrix materials, and the particle suspension sprayed or dip-coated directly onto the balloon surface and dried. In this way the form of the crystals is not affected. Because the particles remain intact the residence time after delivery will be more predictable and dependent on an analysis of the particles that can be done before the balloon is prepared.

Another method of application of the drug particles is to use electrostatic attraction. For instance, a balloon made of a suitable polymeric material (such as a nylon, PET or Pebax® resin) is provided with an electrostatic charge in a manner similar to a van de Graaf generator. The nanocrystalline drug particle powder, is sprayed on a Teflon surface as an aqueous suspension and then dried. The charged balloon is swept just above the powdered surface to attract a coating of the dried powder.

The amount of drug that would be needed is such that a multi-layer of nanoparticles should be deposited on the balloon. Current 1st generation designs of paclitaxel delivery balloons have a payload of 3 microgram/mm$^2$ of which by the way up to 80% is lost during tracking the catheter through the artery. In some embodiments a drug coating of paclitaxel on a balloon contains from 100 to 1000 μg of paclitaxel, for instance 200-800 μg, 300-600 μg, or 400-500 μg of paclitaxel. These dosages may require a coating depth on the balloon of as much as 3 micrometers, or more.

There are various ways to increase the payload a balloon surface could carry drug particles to provide a desirable payload of the drug on the balloon surface. As already mentioned, an excipient can be dissolved in an aqueous media in which the drug particles are suspended. When the combined solution/suspension is dried the excipient forms a matrix in which the particles are held. The matrix allows for a relatively thicker loading of particles. At the time of delivery the matrix material readily dissolves leaving the particles at the tissue site.

Figure 3:
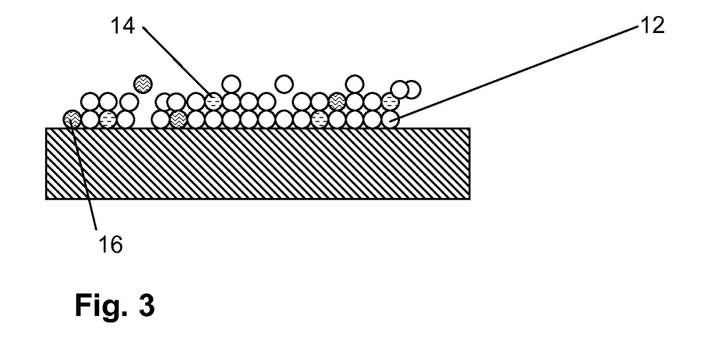
FIG. 3 Schematic depiction of a balloon surface coated with nanocrystalline drug particles and two types of tracer particles.
Figure 4:
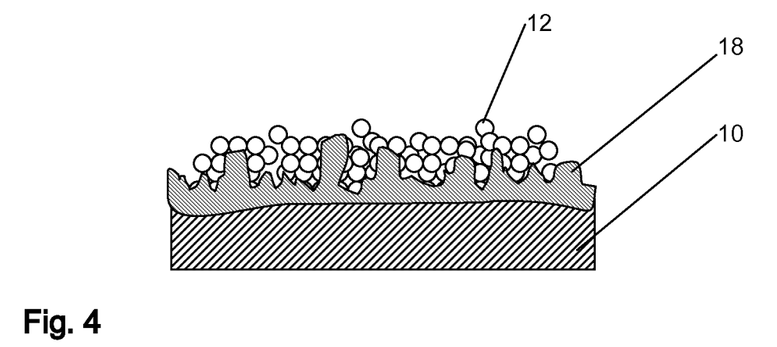
FIG. 4 Schematic depiction of a balloon surface coated with microfibrous rough surface and with nanocrystalline drug particles and tracer particles.

Another way to increase the drug particle loading involves texturizing the balloon surface. Instead of a smooth balloon surface, one can provide the balloon surface with a micro-rough (textured) surface, for example by spraying an initial polymer onto the balloon surface which leaves a rough permanent surface behind. This textured surface will remain permanent on the balloon surface. Illustrative are very soft urethane or silicon surfaces. FIG. 3 is illustrative. The balloon substrate material 10 is provided with a rough texture coating 18, the roughened texture providing crevices which allow retention of a relatively larger number of drug particles 12 on the surface. The surface particles, of course, may optionally include tracer particles not shown in this Figure.

A rough texture balloon surface can be created by using for example a inkjet printing system to provide the coating 18 at varied thickness. Another technique may be to dip-coat the balloon with a liquid composition after which the still-wet surface is blown dry by a strong air jet to provide a roughness produced by the turbulence of the air jet. Curable systems that are applied in a similar textured manner as liquids and then cured to permanently fix the texture are suited for providing such a textured coating 18, as are techniques involving use of polymer solutions in solvent that are set by evaporation.

In at least some embodiments the particles are applied subsequent to texturizing the device surface. However, in some circumstances, for instance if drug particles can be maintained in particulate suspension in a texture-forming composition, and also the cured or set texture matrix does not bond to the particles, a single application of a combination texture material and particle-containing composition may be practical for both texturizing the surface and loading that surface with the drug particles.

In yet another way to increase the drug particle loading, in between the spraying of the nano-particles on the balloon one can spray, alternatingly or simultaneously, secondary materials that act as a matrix material able to quickly dissolve in the body. The excipient materials discussed above are illustrative of such secondary materials. The solvent for this secondary material again should be one that does not dissolve the drug particles. The secondary excipient material so applied may penetrate between the particles or form a cap layer over the particles, depending on application technique, the concentration and viscosity of the applied composition, and the like.

Figure 5:
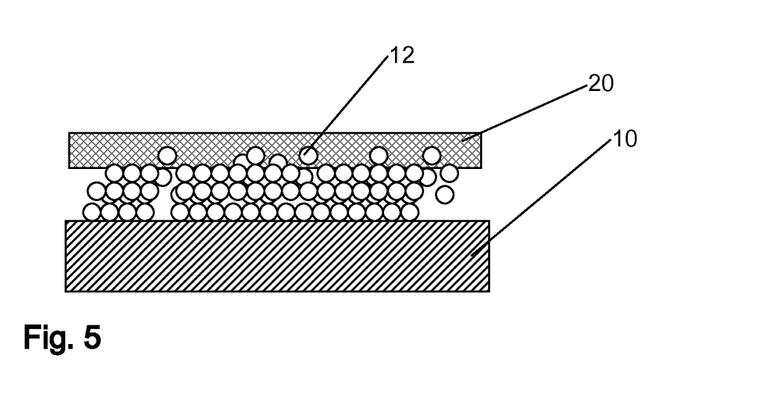
FIG. 5 Schematic depiction of a balloon surface coated with nanocrystalline drug particles and capped with brittle or soluble layer.

FIG. 5 illustrates a specific embodiment of the use of a secondary excipient material applied as top layer 20 on the layer of drug particles 12 to act a breakable lid. In some embodiments such a cap layer may have a thickness of 2 µm or less, for instance about 1 µm, about 0.5 µm, about 0.1 µm, or about 0.01 µm. Polymers or copolymers that have a good solubility in water and a molecular weight sufficient to slow dissolution of the coating enough to provide practical protection may be used. Other protective cap layers may be effective if they break up into fine particles upon balloon expansion. Protective cap layer thickness may be adjusted to give an acceptable dissolution and/or degradation profile.

In still another technique for increasing drug particle loading on a balloon surface, one can combine fibrinogen with the nanocrystals to provide an intertwined network of fibers and particles.

Another application technique is to spray a network of polymer fibers on the balloon surface by electrostatic spray methods producing a very open network. This fiber network can then be dipped in the suspension of the drug nanoparticles.

Although the invention has been described specifically as applied to balloon surfaces, it should be noted that the application techniques may be applied to produce drug particle coatings on other devices adapted for insertion into the body, for instance on permanent implants such as stents, grafts, neurocoils etc.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A drug delivery balloon adapted for delivery of a drug to a site in a body passageway, the balloon comprising a balloon wall with an outer surface, and the balloon having a drug disposed on the outer surface, wherein the drug includes a plurality of crystalline drug particles provided directly on and contacting an outer surface of the balloon, wherein the crystalline drug particles comprise paclitaxel, the crystalline drug particles having a predetermined size distribution, wherein said size distribution is in a range of from 0.01 µm to 0.1 µm, wherein the crystalline drug particles are present in mixture with a water soluble excipient material, wherein the water soluble excipient material forms a fibrous matrix holding the crystalline drug particles, wherein a plurality of non-radioactive tracer particles are mixed with the crystalline drug particles, wherein the non-radioactive tracer particles are detectable by one or more of X-Ray, magnetic resonance imaging, or ultrasound.

2. A drug delivery balloon as in claim 1 wherein said crystalline drug particles comprise at least 95% by weight of said drug.

3. A drug delivery balloon as in claim 2 wherein said crystalline drug particles comprise an anti-agglomeration agent in an amount of less than 1% by weight.

4. A drug delivery balloon as in claim 1 wherein the tracer particles are admixed with drug particles on the balloon.

5. A drug delivery balloon as in claim 4 wherein said tracer particles are of similar size distribution and in a predetermined ratio whereby the amount of drug delivered to the site can be estimated on the basis of detection of the tracer particles.

6. A drug delivery balloon as in claim 4 comprising a plurality of different tracer particles that differ in the manner that they are detectable.

7. A drug delivery balloon as in claim 1 wherein said excipient is a member of the group consisting of water soluble polymers, sugars, polysaccharides, contrast agents, citrate esters, and pharmaceutically acceptable salts.

8. A drug delivery balloon as in claim 1 wherein the balloon comprises textured surface that provides increased particle retention.

9. A drug delivery balloon as in claim 1 wherein the balloon has a capping layer over crystalline drug particles that is water soluble and biodegradable and that breaks free from the balloon upon balloon expansion.

10. A drug delivery balloon as in claim 1 having an amount of crystalline dihydrate paclitaxel on the balloon of from 50 to 1000 µg.

11. A drug delivery balloon comprising a coating thereon and a drug applied over the coating, wherein the coating has a textured surface that increases the drug carrying capacity of the balloon, wherein the drug is provided as crystalline particles free from a polymeric material along an outer surface of the crystalline particles, the crystalline particles are held in a fibrous matrix defined by a water soluble excipient material, wherein the crystalline particles having a predetermined size distribution in a range of from 0.01 µm to 0.1 µm, wherein a plurality of non-radioactive tracer particles are mixed with the crystalline particles.

12. A drug delivery balloon as in claim 11 wherein said coating is formed of a soft silicone or urethane material.

* * * * *